United States Patent [19]

Silbering et al.

[11] Patent Number: 4,965,203

[45] Date of Patent: Oct. 23, 1990

[54] PURIFIED THROMBIN PREPARATIONS

[75] Inventors: Steven B. Silbering, Forest Hills, N.Y.; Rowland P. Blythe, Jr., Washington, Mich.; Russell U. Nesbitt, Jr., Somerville; Mahdi B. Fawzi, Flanders, both of N.J.

[73] Assignee: Warner-Lambert Company, Morris Plains, N.J.

[21] Appl. No.: 365,470

[22] Filed: Jun. 13, 1989

Related U.S. Application Data

[63] Continuation-in-part of Ser. No. 7,555, Jan. 28, 1987, abandoned.

[51] Int. Cl.$^5$ .......................... C12N 9/96; C12N 9/74; A61F 13/00; A61K 37/547
[52] U.S. Cl. ..................................... 435/188; 435/214; 424/446; 424/94.64; 128/156; 128/DIG. 22
[58] Field of Search ................. 435/214, 188; 424/445, 424/446, 94.64; 128/156, DIG. 22

[56] References Cited

U.S. PATENT DOCUMENTS 4,363,319 12/1982 Altshuler ............................ 128/156
4,515,637 5/1985 Cioca ..................................... 424/94
4,696,812 9/1987 Silbering et al. .................... 424/445

OTHER PUBLICATIONS

Baughman, D. J. (1970) Met. in Enzymology 19, 145–157.

Primary Examiner—Elizabeth C. Weimar
Assistant Examiner—Charles L. Patterson
Attorney, Agent, or Firm—Ronald A. Daignault

[57] ABSTRACT

Improved thrombin formulations, stable at room temperature using stabilizing quantities of a polyol and a buffer at specific pHs are described wherein crude thrombin is first purified by two-stage ion exchange chromatography.

4 Claims, No Drawings

PURIFIED THROMBIN PREPARATIONS

CROSS-REFERENCE TO RELATED APPLICATIONS

This application is a continuation-in-part of U.S. application Ser. No. 007,555 filed Jan. 28, 1987, abandoned.

BACKGROUND

Thrombin, a proteolytic enzyme, is essential or hemostasis. It is a principal reagent in the formation of blood clots via fibrin production. Due to its effectiveness as a clotting aid, thrombin and its preparations are useful during surgical procedures to control bleeding. While dry thrombin is available, liquid preparations are generally preferred due to handling and time considerations.

Until now, there have been no highly stable liquid thrombin preparations which are both storage stable and ready for use during surgery. This is because thrombin, when dissolved in water or saline, rapidly loses its activity due to denaturation and autolysis of the thrombin protein.

THE INVENTION

It has been discovered that when thrombin is purified by passage through a series of ion-exchange columns, and then formulated with a polyol and certain buffers in a medium of particular ionic strength, the resulting formulation will have superior stability to a similar formulation prepared with unpurified thrombin. For example, in one preferred embodiment, a solution containing 1500 NIH units/ml of purified thrombin in 0.45 M sodium chloride, 0.05 M acetate buffer, 25% (v/v) glycerol, was prepared at pH 5.0. This solution retained more than 85% of its original activity after storage at 25° C. for six months. This represents a considerable improvement over a formulation identical in all respects, except that the thrombin was not purified. In this case, the formulation though considerably more stable than a solution in which thrombin is dissolved in physiological saline, retained only 71% of its original activity after storage at 25° C. for one month. Therefore, the use of purified thrombin substantially extends the shelf-life of the thrombin formulation described in U.S. Pat. No. 4,696,812.

It has also been discovered that sterile, storage stable thrombin preparations can be produced by adding to purified thrombin, in a suitable medium, stabilizing quantities of certain buffers. Optionally, saline and one or more polyol stabilizers can also be employed.

In one preferred embodiment, a solution containing 2,000 U/ml (units per milliliter purified thrombin in 0.45 M NaCl solution containing 50% (v/v) glycerol and 0.05 M phosphate buffer, pH 6.0, was prepared. This solution, after storage at room temperature (25° C.) for 6 months, had retained all of its original clotting activity. After storage for 12 months at room temperature, this solution still retained 80% of its original activity.

These preferred compositions showed even better activity retention when stored at 4° C., i.e., 100% for the phosphate system after 12 months and 95% for the acetate system after 12 months.

ADVANTAGES

The thrombin compositions and methods of the invention have several advantages over conventional preparations and methods for assisting in blood clotting.

Unlike powdered preparations, the compositions of the instant invention require no reconstitution prior to use. Thus, measuring, mixing, sterilizing, etc. of one or more component(s) or container(s) are not important considerations. The instant preparations can be used with only minimal, i.e., little or no, preparation before final use.

Furthermore, the stability of the instant thrombin-containing materials is such that the need for stock inventories and/or rotation of products is largely eliminated. Unlike most saline or water-solutions of thrombin, which are stable for only about 1 week at 4° C., the instant preparations are designed to be stable at normal refrigeration temperatures (i.e., about 4° C) and at room temperature (i.e., about 25° C.) for 6 months or more.

It is known that high concentrations of glycerol, sucrose, and other polyols can stabilize proteins in solution. In the case of thrombin, it is known that a glycerol concentration of 67%, can greatly stabilize a 1,000 $\mu$/ml thrombin solution. However, use of high glycerol concentrations is not practical in the large scale manufacture of a sterile thrombin solution because of the high viscosity of such a preparation. The instant compositions, which contain 50% or less, of glycerol avoid these problems.

Other advantages and aspects of the invention will become apparent from a consideration of the following description of the invention.

DESCRIPTION OF THE INVENTION

The invention concerns, in its broadest aspects:

I. A liquid composition containing substantially purified thrombin, in combination with a definite range of salts, buffer and a polyol.

II. Coagulant products useful as dressings which contain the preparations of I.

III. Methods of making the thrombin compositions of I.

The preparations made in accordance with the invention must contain, in an aqueous medium, purified thrombin, and one or more of the buffers of the invention and a polyol. They may contain saline, and other substances conventionally employed in protein preparations.

While the term "preparations" is employed, it should be noted that applicants contemplate all types of formulations in which thrombin, in substantially solubilized or highly dispersed form, is present in combination with one of more of the instant glycols and buffers.

Liquid preparations are generally preferred. Solutions of thrombin are highly preferred. When a liquid formulation is made, it is generally preferred that the solvent(s) or other diluent(s) employed have a suitable miscibility with thrombin such that production standards, e.g., uniformity of thrombin concentration from batch to batch, can be readily met.

The thrombin employed is a purified thrombin obtained by a two-stage ion-exchange chromatography. In the first stage, DEAE Sepharose®, a 2-(diethylamino)ethyl ether of agarose, available from Pharmacia Fine Chemicals, Inc., is employed to adsorb a large portion of the non-thrombin protein. In the second stage, CM-Sepharose®, a carboxymethyl ether of agarose, available from Pharmacia Fine Chemicals, Inc., is employed to adsorb thrombin and allow the remaining non-thrombin protein to pass through the column. The thrombin is eluted from the column by using either 0.05 M acetate in 0.45 M NaCl, pH 5.0 or by using 0.05 M phosphate in 0.45 M NaCl, pH 6.0. This thrombin solution is then mixed with glycerol containing either acetate buffer or phosphate buffer and saline, in order to prepare the stabilized solution described as the invention.

Thrombin is known to be soluble in physiological saline—i.e., a solution containing about 0.9% NaCl in water. However, other saline solutions are contemplated as useful herein. Furthermore, the replacement of all or part of the NaCl in such solutions with one or more other suitable salts is contemplated.

Water is a preferred medium for the preparations of the invention. However, the use of one or more other diluents which do not adversely affect the solubility and/or stability of thrombin in the subject preparations is desirable.

One such diluent is glycerol. Other useful polyols include mannitol, sorbitol, sucrose, glucose, and the like. Mixtures are operable. Glycerol is highly preferred.

The glycerol or other polyol ingredient(s) will be employed at a total concentration of from about 10 to about 60 wt %, preferably 25 to 50 wt % based on total composition weight.

Unless stated otherwise, all quantities recited are weight percentages based on total compositions weight.

Buffer systems have been found to be essential to maintain the pH of the final thrombin solution between about 5.0 and about 8.0, with a preferred pH range of about 5.0 to about 6.5. It is highly preferred that when a phosphate buffer is used the final pH of the preparation be about 6.0 to about 6.5 and when an acetate buffer is used, the final pH be about 5.0.

pH measurements are made using an ordinary pH meter with a combination electrode.

Useful buffer systems include acetate, phosphate, succinate, bicarbonate, imidazole, TRIS, and the zwitterionic buffers described by N. E. Good and S. Izawa, in *Methods in Enzymol.*, 24, Part B, 53 (1972); and W. F. Ferguson, K. I. Braunschweiger, W. R. Braunschweiger, J. R. Smith, J. McCormick, C. C. Wasmann, N. P. Jarvis, D. H. Bell and N. E. Good in *Anal. Biochem.*, 104, 300 (1980). These disclosure are hereby incorporated by reference.

Suitable reagents for use in the instant buffer systems include MES, ACES, BES, MOPS, TES, HEPES and the like. Phosphate should only be used when calcium ion is absent or in the presence of EDTA. Mixtures of such reagents can be employed. If mixed buffers are used, the final pH should be suitably adjusted. Buffers containing phosphate ion and acetate ions are preferred. Mixtures are operable.

The buffer systems disclosed in U.S. Pat. No. 4,696,812 can also be employed herein.

The buffers will be present in the buffer solution, along with water and/or other suitable diluent(s) at total concentrations of about 0.02 M to about 1 M, preferably about 0.05 M to about 0.10 M.

The use of various other conventional additives, e.g., antioxidants, colorants, surfactants, and the like, is also contemplated. Glutathione may be employed as an optional ingredient. Amino acids may be employed as optional ingredients, but their presence must not be in such quantities as to interfere with the stabilizing action of the polyol and buffer components on the purified thrombin. In general, it is preferred that they be used in only minute quantities at concentrations of 0.5% or less, if at all.

In general, the concentration ranges for the ingredients discussed above will be within the limits set out in Table I. Percentages are based on total composition weight.

TABLE I

| Ingredient | Broad | Preferred | Highly Preferred |
|---|---|---|---|
| Thrombin (units/ml) | 10–10,000 | 50–5,000 | 100–2,000 |
| Sodium Chloride (wt/v, %) | 0–5 | 0–2.7 | 0.9–2.7 |
| Polyol (v/v, %) | 0–60 | 10–50 | 25–50 |
| Buffer (molarity) | 0.01–1.0 | 0.02–0.20 | 0.05–0.10 |

Hemostatic materials, such as GELFOAM ®, SURGICEL ®, and AVICEL ®, and collagen which are presently used alone or in combination with thrombin powder or thrombin in saline, can be effectively used with the stabilized thrombin formulations of the present invention using a variety of techniques. Preferably, the stabilized solution is absorbed onto the hemostatic agent and the pad is freeze-dried and packaged in a sterile manner.

Antimicrobial or antibiotic agents can also be incorporated into such pads, especially for use on burn patients, where prevention of infection is critical. In addition, surfactants and salts other than NaCl can be employed. When one or more of such additives are present, their concentrations are generally within the ranges set out in Table II.

TABLE II

| | | Weight Percentage | |
|---|---|---|---|
| Additive | Broad | Preferred | Highly Preferred |
| Surfactants | 0–2 | 0–0.5 | 0–0.2 |
| Antioxidants | 0–1 | 0–0.2 | 0–0.1 |
| Antimicrobials | 0–1 | 0–0.5 | 0–0.2 |
| Other additives e.g., salts | 0–5 | 0–3 | 0–1 |

One type of bandage suitable in the preparation of coagulants in accordance with the invention is set forth in U.S. Pat. No. 4,363,319, the disclosure of which is hereby incorporated by reference.

PRODUCTION OF PURIFIED THROMBIN PREPARATIONS

A solution of bovine thrombin, in which the thrombin was purified by passage through a DEAE-Sepharose ® column, followed by passage through a CM-Sepharose ® column, has a potency of 8000 units/ml. In addition to thrombin, this solution contains sodium chloride at a concentration of 2.7% and phosphate buffer at a concentration of 0.05 M. The pH of the solution is 6.0. To one liter of this solution is added four liters of glycerol, followed by a solution adjusted to pH 6.0, containing 184.12 grams of sodium chloride and 47.63 grams of potassium phosphate monobasic in two liters of distilled water. The volume of the thrombin formulation is then adjusted to 8.0 liters with distilled water. The pH of the solution is adjusted to 6.0 if necessary. The potency of this solution should be approximately 1000 units/ml.

The resulting preparation is assayed by measurement of clotting time using a BBL fibrometer.

The invention is illustrated by the following example(s).

EXAMPLE 1

The preparation of phosphate-buffered thrombin composition is given above. An acetate-buffered composition would be prepared in a similar manner, by substituting 0.05 M acetate, pH 5.0, for 0.05 M phosphate, pH 6.0.

Thrombin compositions of the present invention are assayed by the following procedure:

The thrombin activity levels are determined by measurement of clotting time on a BBL fibrometer. The source of fibrinogen is pooled human plasma diluted 1:1 with 0.9% saline. The thrombin solution is diluted 200-fold with 0.5% polyethylene glycol 8000 in imidazole buffered saline. Into a coagulation cup is added 0.2 ml of diluted plasma. This is kept at 37° C. for 3 minutes, and to this solution is added 0.1 ml of diluted thrombin solution, which has also been kept at 37° C. for 3 minutes. Clotting time is determined directly from the fibrometer reading. The number of thrombin units/ml remaining is determined from a standard curve of thrombin concentration vs. clotting time.

EXAMPLE 2

The data in Table III illustrates the stability of purified thrombin in a glycerol-phosphate system, pH 6.0.

TABLE III

Solution Stability of Purified Thrombin (2,000 Units/ml) at 4° and 25° C. in Various Glycerol-Phosphate (0.45 M NaCl, 0.05 M Phosphate, pH 6.0) Formulations

| Temp. (C.°) | Storage Time (Months) | | Test Formulation % of Activity | | | |
|---|---|---|---|---|---|---|
| | | | A | B | C | D |
| | | Glycerol | 50% | 25% | 10% | — |
| 25 | 0 | | 100 | 100 | 100 | 100 |
| | 1 | | 93 | 98 | — | — |
| | 2 | | 87 | 96 | — | — |
| | 3 | | 104 | 96 | — | — |
| | 4 | | — | — | 45 | 20 |
| | 6 | | 105 | 81 | — | — |
| | 12 | | 80 | 25 | — | — |
| 4 | 0 | | 100 | 100 | 100 | 100 |
| | 1 | | 92 | 108 | 82 | 88 |
| | 2 | | 90 | 110 | 87 | 78 |
| | 3 | | 88 | 109 | 96 | 79 |
| | 6 | | 106 | 115 | 101 | 62 |
| | 12 | | 106 | * | 71 | 27 |

*Contaminated

It should be noted that thrombin stability is not maintained at room temperature when the level of glycerol is lower than 25%.

EXAMPLE 3

The data in Table IV illustrates the stability of purified thrombin in a glycerol-acetate system, pH 5.0.

TABLE IV

Solution Stability of Purified Thrombin (1,500 Units/ml) at 4° and 25° C. in 25% Glycerol-Acetate Formulations

| Temp. (C.°) | Storage Time (Months) | NaCl Acetate pH | Test Formulation % of Activity | |
|---|---|---|---|---|
| | | | A | B |
| | | | 2.7% 0.05 M 5.0 | 2.7% 0.10 M 5.0 |
| 4 | 0 | | 100 | 100 |
| | 1 | | 94 | 91 |
| | 2 | | 102 | 108 |
| | 3 | | 102 | 102 |
| | 6 | | 100 | 110 |
| | 12 | | 95 | 96 |
| 25 | 0 | | 100 | 100 |
| | 1 | | 102 | 102 |
| | 2 | | 98 | 98 |
| | 3 | | 89 | 87 |
| | 6 | | 86 | 91 |
| | 12 | | 56 | 57 |

It is instructive to compare the stabilities of impure and purified thrombins in similar formulations. A solution of impure thrombin (1500 units/ml in 25% (w/w) glycerol, 0.05 M acetate, 0.45 M NaCl, having a pH of 5.0, when stored at 25° C. for 1 month, was found to retain 68% of its initial clotting activity. A similar formulation, containing 1,500 units/ml purified thrombin, was found to retain 100% of its initial activity after 1 month at 25° C., and was found to retain 86% of its activity after 6 months at 25° C.

EXAMPLE 4

Preparation of a hemostat.

A GELFOAM ® pad is saturated with a solution of purified thrombin in 0.05 M acetate buffer, pH 5.0% containing 0.45 M saline. GELFOAM ® is a heterogeneous mixture of water-soluble proteins of high average molecular weight in gelatin form and is available from the Upjohn Company. The pad is freeze-dried. Thrombin contained in such a dry pad can maintain its stability for prolonged periods, even at room temperature. It was found that pads of GELFOAM ®, saturated with purified thrombin in glycerol/acetate, and stored in the wet state, completely disintegrated in 6 days at room temperature.

Reasonable variations, such as those which would occur to a skilled artisan, can be made herein without departing from the scope of the invention.

We claim:

1. In a method of preparing a stable thrombin composition consisting essentially of thrombin, 25–50% of a polyol and a buffer of acetate or phosphate ions, the improvement consisting of further purification of the thrombin comprising:
   (a) adsorbing the thrombin on a DEAE agarose column,
   (b) eluting the thrombin from the said DEAE agarose column with 0.45 M buffer in 0.45 M NaCl,
   (c) adsorbing the eluate of step (b) on a CM agarose column and,
   (d) eluting the thrombin from the said CM agarose column with 0.45 M buffer in 0.45 M NaCl.

2. The method of claim 1 wherein the polyol is glycerol.

3. The method of claim 1 wherein the buffer of the said stable thrombin composition is a phosphate buffer and the final pH is about 6.0 to about 6.5.

4. The method of claim 1 wherein the buffer of the said stable thrombin composition is an acetate buffer and the final pH is about 5.0 to about 5.5.

* * * * *